(12) United States Patent
Wood et al.

(10) Patent No.: US 6,670,607 B2
(45) Date of Patent: Dec. 30, 2003

(54) CONDUCTIVE POLYMER COATED NANO-ELECTROSPRAY EMITTER

(75) Inventors: Troy D. Wood, Kenmore, NY (US); E. Peter Maziarz, III, Brockport, NY (US); Sarah A. Lorenz, Honolulu, HI (US); Thomas P. White, Buffalo, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 141 days.

(21) Appl. No.: 09/754,736

(22) Filed: Jan. 4, 2001

(65) Prior Publication Data

US 2002/0003209 A1 Jan. 10, 2002

Related U.S. Application Data

(60) Provisional application No. 60/174,548, filed on Jan. 5, 2000.

(51) Int. Cl.[7] .............. B01D 59/44; H01J 49/00; F02D 1/06; F02D 7/00; F23D 11/10; F23D 11/40; F23D 14/62; F23D 11/32; B05B 5/00
(52) U.S. Cl. .............. 250/288; 250/281; 250/282; 250/423 F; 239/5; 239/418; 239/708; 216/92; 106/162.51; 435/173.1
(58) Field of Search ............................ 250/281, 282, 250/288, 423 F; 239/5, 418, 708; 204/452; 435/173.1; 106/162.51

(56) References Cited

U.S. PATENT DOCUMENTS

| 5,115,131 | A | * | 5/1992 | Jorgenson et al. .......... 250/282 |
| 5,235,186 | A | | 8/1993 | Robins |
| 5,292,792 | A | | 3/1994 | Carew |
| RE34,757 | E | * | 10/1994 | Smith et al. ........... 106/162.51 |
| 5,423,964 | A | | 6/1995 | Smith et al. |
| 5,543,618 | A | * | 8/1996 | D'Silva ....................... 250/288 |
| 5,572,023 | A | * | 11/1996 | Caprioli ...................... 250/288 |
| 5,716,550 | A | * | 2/1998 | Gardner et al. ............. 252/500 |
| 5,747,799 | A | | 5/1998 | Franzen |
| 5,753,910 | A | * | 5/1998 | Gourley et al. ............. 250/281 |
| 5,788,166 | A | * | 8/1998 | Valaskovic et al. ......... 239/708 |
| 5,917,184 | A | * | 6/1999 | Carson et al. .............. 250/288 |
| 5,945,678 | A | * | 8/1999 | Yanagisawa ............ 250/423 F |
| 5,968,674 | A | * | 10/1999 | Hsieh et al. ........... 252/519.33 |
| 5,993,633 | A | | 11/1999 | Smith et al. |
| 5,993,694 | A | * | 11/1999 | Ito et al. ..................... 252/500 |
| 5,994,696 | A | * | 11/1999 | Tai et al. .................... 250/288 |
| 6,032,876 | A | * | 3/2000 | Bertsch et al. .............. 239/418 |
| 6,068,749 | A | * | 5/2000 | Karger et al. ............... 204/452 |
| 6,093,557 | A | * | 7/2000 | Pui et al. ................. 435/173.1 |
| 6,107,628 | A | | 8/2000 | Smith et al. |
| 6,136,212 | A | * | 10/2000 | Mastrangelo et al. ......... 216/27 |
| 6,139,734 | A | | 10/2000 | Settlage et al. |
| 6,187,214 | B1 | * | 2/2001 | Ganan-Calvo ............... 216/92 |
| 6,189,803 | B1 | * | 2/2001 | Ganan-Calvo ................. 239/5 |
| 6,284,072 | B1 | * | 9/2001 | Ryan et al. ................. 156/209 |
| 6,297,499 | B1 | * | 10/2001 | Fenn .......................... 250/288 |
| 6,410,915 | B1 | * | 6/2002 | Bateman et al. ............ 250/281 |

* cited by examiner

Primary Examiner—John R. Lee
Assistant Examiner—Mary El-Shammaa
(74) Attorney, Agent, or Firm—Nixon Peabody LLP (57) ABSTRACT

The present invention relates to a nanospray emitter including an emitter body which includes a fluid inlet, an outlet orifice, and a passage communicating between the fluid inlet and outlet orifice; and an electrically conductive polymer coating on at least a portion of the emitter body. Also disclosed are a nano-electrospray device including the nanospray emitter of the present invention, a method for making a nanospray emitter of the present invention, a method of forming a nanospray using the nanospray emitter of the present invention, and a method of analyzing a solution using the nanospray emitter of the present invention.

35 Claims, 6 Drawing Sheets

CONDUCTIVE POLYMER COATED NANO-ELECTROSPRAY EMITTER

This application claims the benefit of U.S. Provisional Patent Application Ser. No. 60/174,548 filed Jan. 5, 2000, which is hereby incorporated by reference in its entirety.

FIELD OF THE INVENTION

The present invention generally relates to nano-electrospray emitters, nano-electrospray devices containing such emitters, methods of making such emitters, and use thereof.

BACKGROUND OF THE INVENTION

Electrospray ionization ("ESI") (Whitehouse et al., 1985; Meng et al., 1988) has revolutionized the use of mass spectrometry in bioanalytical chemistry because of its ability to transfer large macromolecules from solution into the gas-phase as intact multiply-charged molecular ions. A special advantage of ESI is the ease with which it may be coupled to liquid chromatography ("LC") (Banks, 1995), capillary electrophoresis ("CE") (Smith et al., 1993), and capillary electrochromatography ("CEC") (Schmeer et al., 1994). In the last five years, a number of research groups have developed methods for decreased sample consumption in ESI by using much lower flow rates (nL/min) than with conventional ESI ($\mu$L/min) (Emmett and Caprioli, 1994; Kriger et al., 1995; Valaskovic et al., 1995a; Kelly et al., 1997; Wilm and Mann, 1996). Of these low flow ESI methods, the flow rate is controlled by some type of pump in microspray (Emmett and Caprioli, 1994), whereas in nanospray the flow rate is controlled by the potential difference between the emitter and counter-electrode (Wilm and Mann, 1996). Typically, nanospray has been accomplished by pulling silica or glass substrates under heat to produce tapered emitters with small inner diameters, e.g., a few $\mu$m. Attomole level sample consumption has been achieved using nanospray (Valaskovic et al., 1995a; Valaskovic et al., 1996a).

While nanospray provides an avenue to achieve low-level detection limits with MS using only a few $\mu$L of sample, even at high salt and/or buffer concentrations, most nanoliter-flow ESI emitters suffer from short operating lifetimes, poor durability, and/or low reproducibility. For example, metallized coatings have been applied to emitter substrates to provide electrical contact at the ESI outlet, but such emitters are highly susceptible to deterioration by electrical discharge (Valaskovic et al., 1995a).

To overcome this serious limitation, methods to increase metallized emitter lifetime in nanospray have been developed. These include chemical derivatization of an organo-functional silane on the emitter substrate prior to metallization (Kriger et al., 1995), by depositing a $SiO_x$ overcoating atop the metallized layer (Valaskovic et al., 1996b), or by controlled electrochemical deposition of metal film onto the emitter substrate (Kelly et al., 1997). Though these multi-layer and electrolysis methods have shown improvement in emitter durability for low flow ESI, they are tedious and time-consuming. Alternatively, nonmetallized emitters have been employed with low flow ESI by remotely coupling the ESI voltage to the emitters (Emmett et al., 1998; Hannis and Muddiman, 1998). A disadvantage of this approach, however, is that it relies on the conductive properties of the solution used, rather than the conductive properties of the emitter itself. Solution conditions may vary widely for both LC and capillary separations, and such emitters may exhibit wide differences in performance depending upon the mobile phase conditions used in the separation. Placing a metal wire into the tip for electrical contact has proved beneficial for durability (Kelleher et al., 1997; Cao and Moini, 1997; Fong and Chan, 1999), however it would be preferable to avoid the need to regulate the insertion, removal, or adjustment of an independent metal wire.

As stated by Lausecker et al., a good, long-acting and stable electrical contact on the CZE capillary terminus remains the main challenge (Lausecker et al., 1998) in performing MS coupled to capillary separations. Thus, to fully exploit the advantages of nanospray-MS with CE for the purposes of molecular species identification of analytes in biological fluids (i.e., at sub-picomole levels), a stable and/or reproducible type of nanospray emitter must be developed.

For nanospray ESI-MS emitters to be useful in coupling to either CE or CEC, the emitters must remain stable throughout the separation process. Failure of the emitter during the course of the separation is not acceptable. For quantification in particular, if calibration curves of multiple analytes at multiple concentration levels are to be constructed, single emitters with longer lifetimes or multiple emitters showing reproducible performance and ionization efficiency are needed.

The present invention is directed to overcoming these deficiencies in the art.

SUMMARY OF THE INVENTION

One aspect of the present invention relates to a nanospray emitter including an emitter body which includes a fluid inlet, an outlet orifice, and a passage communicating between the fluid inlet and outlet orifice; and an electrically conductive polymer coating on at least a portion of the emitter body.

A further aspect of the present invention relates to a nano-electrospray device including a counter-electrode and a nanospray emitter of the present invention whose inlet is capable of fluid communication with a fluid source including a fluid containing one or more analytes. Either the counter-electrode or the nanospray emitter can be either coupled to a power supply, with the other being grounded, for development of a suitable electrical potential between the counter-electrode and the nanospray emitter, which causes the fluid to be drawn through the passage of the nanospray emitter for discharge from the outlet orifice.

Yet another aspect of the present invention relates to a method for making a durable nanospray emitter. This method includes the steps of providing a nanospray emitter body comprising a fluid inlet, an outlet orifice, and a passage communicating between the fluid inlet and outlet orifice; and casting a thin film of an electrically conductive polymer coating onto at least a portion of the nanospray emitter body.

A still further aspect of the present invention relates to a method of forming a nanospray of a solution which includes passing a solution including an analyte through a nanospray emitter of the present invention under conditions effective to electrically charge the solution in a manner to emit the solution from the emitter in the form of a nanospray.

Another aspect of the present invention relates to a method of analyzing a solution for an analyte in the solution. This method includes passing a solution including an analyte through a nanospray emitter of the present invention under conditions effective to electrically charge the solution in a manner to emit the solution from the emitter in the form of a nanospray, and then analyzing the nanospray emission in a manner suitable to detect an analyte present in the solution.

The conductive polymer coatings on emitters of the present invention are a significant departure from previously existing nanospray emitter coatings, all of which are based on metals. The conductive polymer-coated nanospray emitters of the present invention overcome the most problematic limitations of metallized emitters: they provide long-term durability while being simple to coat. With respect to a preferred embodiment, polyaniline ("PANI") coated emitters are desirable because the PANI coating is resistant to corrosion (Wessling and Posdorfer, 1999) while maintaining high mechanical stability and antistatic properties (Triveldi and Dhawan, 1992). No PANI contamination is observed in the ESI spectra. Moreover, in its conductive form PANI is optically transparent (green), allowing for direct viewing of the ESI sample, and possesses outstanding adherence to glass properties (Manohar et al., 1991). PANI-coated nanospray emitters are relatively simple to produce and are highly resistant to electrical discharge. The sensitivity enhancement of PANI-coated nanospray emitters is similar to that of gold-coated emitters vs. normal ESI for tested analytes. Because of the significantly greater durability for the PANI coated emitters of the present invention, the emitters are available for use in analyzing, e.g., via CE-MS, highly complex biological matrices including, without limitation, drugs and their metabolites, neuropeptides, neurotransmitters, and biomolecules from complex biological fluids and tissues.

BRIEF DESCRIPTION OF THE DRAWINGS

FIGS. 1A–B illustrate a PANI-coated nanospray emitter of the present invention.

FIGS. 7A–C are nanospray ESI-FT mass spectra of equine cytochrome c (30 μM). FIG. 7B is a nanospray ESI-FT mass spectrum using gold-coated emitters, sum of 10 scans. Total sample consumed=1.3 pmol. FIG. 7C is a nanospray ESI-FT mass spectrum using xylene-soluble PANI dispersions coated onto the emitters, sum of 10 scans. Total sample consumed= 680 fmol.

DETAILED DESCRIPTION OF THE INVENTION

One aspect of the present invention relates to a nanospray emitter which overcomes the previously mentioned deficiencies in the art. The nanospray emitter of the present invention includes an emitter body which includes a fluid inlet, an outlet orifice, and a passage communicating between the fluid inlet and outlet orifice; and an electrically conductive polymer coating on at least a portion of the emitter body.

The emitter body can be formed of any material suitable for use in nanospray emitters, preferably a glass or glass ceramic material. Suitable materials include, without limitation borosilicate glasses and glass ceramics, aluminosilicate glasses and glass ceramics, and fused silica glasses.

Emitter bodies can be pulled from glass or glass ceramic capillary tubes, forming a tapered (e.g., conical) portion of the body which has the outlet orifice at the tip thereof (see Wilm and Mann, 1994). The emitter pulling technique can be performed using a fiber-pulling device (Sutter Instruments) equipped with either a resistance heating element or a $CO_2$ laser. Instruments equipped with a $CO_2$ laser are better adapted for use with more substrates (than those equipped with resistance heating elements); only the $CO_2$ laser is capable of heating fused silica for subsequent pulling. It has been shown that this method exhibits reproducible emitter production with respect to taper geometry and orifice inner diameters (Valaskovic et al., 1995b).

To open the emitter orifice, if necessary or desired, a number of techniques may be used. According to a first approach, HF etching can be performed according to known techniques (Valaskovic et al., 1995b). According to another approach, which is perhaps safer to the operator and, therefore, preferred, a micro-pipette beveler (Sutter Instruments, model BV-10) can be employed to grind the emitter ends in a controlled fashion. Both approaches enable tailoring of the orifice inner diameter. The orifice preferably has an inner diameter of less than about 20 μm, more preferably between about 1 μm to about 5 μm, even more preferably about 3 μm to about 5 μm.

Alternatively, suitable emitter bodies of the type described above can be purchased (in a pre-pulled shape) from various commercial suppliers, including New Objective (Cambridge, Mass.).

The electrically conductive polymer coating can be any suitable polymer coating which (i) has a conductivity of at least about $1.0 \times 10^{-3}$ S/cm (at 25° C.) and (ii) will resist electrical discharge (i.e., and remain electrically conductive) under electrospray conditions for a duration of at least about 1 hour.

The conductivity of the electrically conductive polymer is preferably between about $1.0 \times 10^{-3}$ to about 5 S/cm (at 25° C.).

The durability of the electrically conductive polymer is dependent upon its longevity under normal electrospray conditions. Preferably, the electrically conductive polymer will resist electrical discharge for at least about 3 to 6 hours, more preferably at least about 24 hours, even more preferably several days or more.

Without being bound by theory, it is believed that suitable electrically conductive polymer coatings of the present invention additionally exhibit electrostatic adherence to the glass or glass ceramic substrate. For example, it is believed that PANI coatings possess positively charged sites within the polymer that interact with negatively charged sites on the glass or glass ceramic substrate.

Although not critical, it is desirable for the thickness of the electrically conductive polymer to be substantially uniform over the entire portion of the emitter body which is coated with the polymer. The thickness of the electrically conductive polymer coating is preferably less than about 10 $\mu$m, more preferably between about 2 $\mu$m to about 4 $\mu$m.

The electrically conductive polymer coating can be applied to any portion of the emitter body which will allow for electrical charge to be conveyed to the solution passing through the emitter body. For example, the electrically conductive polymer coating can be applied to a portion of the emitter body adjacent to the inlet thereof (distal end), a portion of the emitter body adjacent to the outlet orifice thereof (proximal end), or substantially the entire emitter body. Depending on the placement of the coating (proximal vs. distal end), the shape of the nanospray plume can be affected. For example, coating at the proximal end typically yields a narrower nanospray plume whereas coating at the distal end typically yields a broader nanospray plume. Under most circumstances, a narrower plume will be desirable to capture (via the inlet of an analytical device such as a mass spectrometer) a greater volume of the nanospray emission.

One preferred electrically conductive polymer is a polyaniline ("PANI") coating. PANI is unique amongst electroactive polymers in that its conductive state is achieved by protonation of N in the polymer backbone, as opposed to p-doping and partial oxidation of the polymer $\pi$ system (Genies et al., 1990). The analytically pure base form of PANI is given in structure (I) below, where the fully reduced state "leucoemeraldine" corresponds to Y=1 and the fully oxidized state "pernigraniline" corresponds to Y=0. When Y=0.5, PANI is said to be in its "emeraldine" oxidation state. Treatment of the "emeraldine" oxidation state of PANI with high acid concentrations (~1 M HCl) leads to the formation of the "emeraldine salt", in which the oxidized repeat units in structure (I) are converted to hydrochloride salt functionalities. It is the emeraldine salt form of PANI that is conductive (MacDiarmid et al., 1987).

The PANI coating is characterized by the following properties: high resistance to electrical discharge, with coatings lasting for several days or more under electrospray conditions; a conductivity of about 5 S/cm at 25° C. and 1 M HCl (MacDiarmid et al., 1987); resistance to corrosion (Wessling and Posdorfer, 1999) while maintaining high mechanical stability and antistatic properties (Triveldi and Dhawan, 1992); optical transparency (green), allowing for direct viewing of the ESI sample; and outstanding adherence to glass properties (Manohar et al., 1991).

Figure 1A:
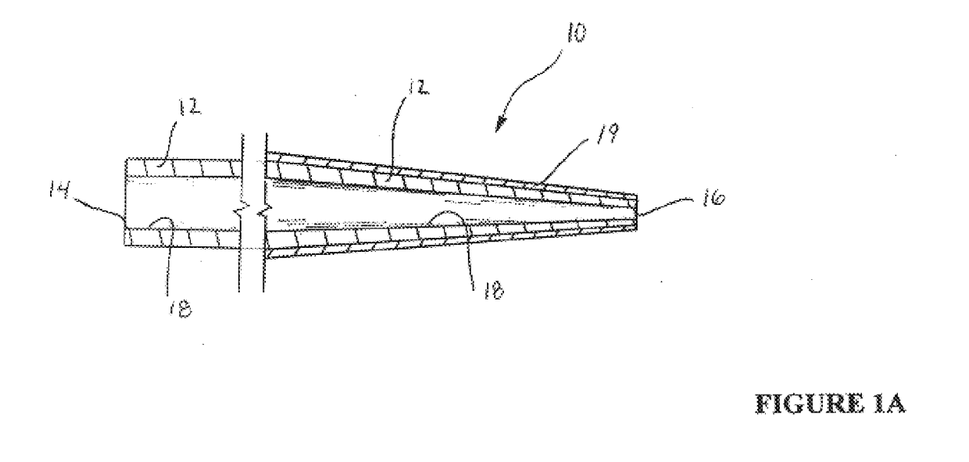
FIG. 1A is a longitudinal cross-sectional view of the PANI-coated nanospray emitter, illustrating the relationship between the emitter body and the PANI coating thereon. The PANI coating is adjacent to the outlet orifice of the emitter body.
Figure 1B:
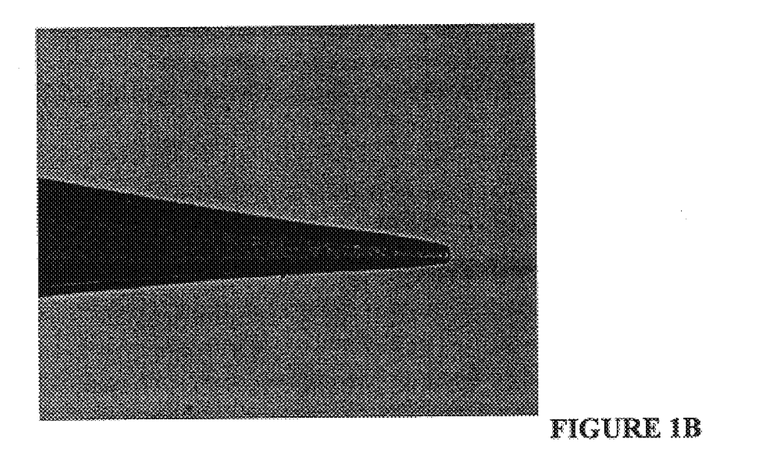
FIG. 1B is an image, prepared by photomicrograph, which illustrates the optical transparency of a water-soluble PANI-coated emitter of the present invention.

One embodiment of the nanospray emitter of the present invention is illustrated in FIG. 1A. The emitter 10 includes a tapered (i.e., conical) body 12 having a fluid inlet 14, an outlet orifice 16, and a passage 18 communicating between the fluid inlet and outlet orifice. Adhered to a portion of the exterior of the body 12 is a PANI coating 19, which extends to the proximal end containing the outlet orifice 16. As shown in FIG. 1B, a nanospray emitter of the present invention, which is coated with a water-soluble PANI coating, is translucent. A translucent emitter enables visual examination of the fluid passing through the passage 18.

Figure 2:
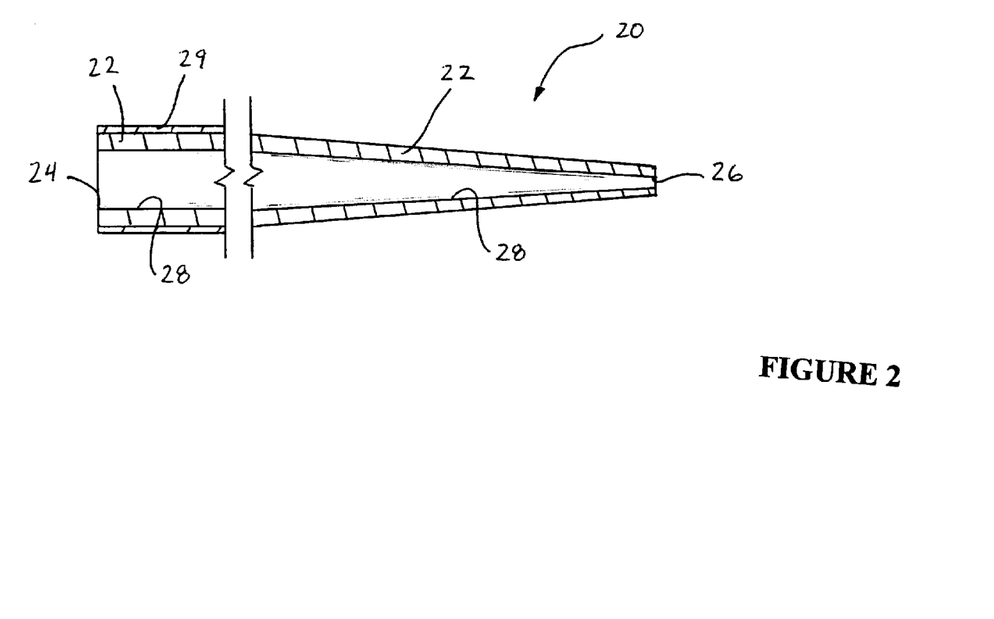
FIG. 2 is a longitudinal cross-sectional view of another embodiment of a PANI-coated nanospray emitter of the present invention. The emitter includes a PANI coating adjacent the inlet to the emitter body.

A second embodiment of the nanospray emitter of the present invention is illustrated in FIG. 2. The emitter 20 includes a tapered (i.e., conical) body 22 having a fluid inlet 24, an outlet orifice 26, and a passage 28 communicating between the fluid inlet and outlet orifice. Adhered to a portion of the exterior of the body 22 is a PANI coating 29, which extends to the distal end containing the inlet 24.

Figure 3:
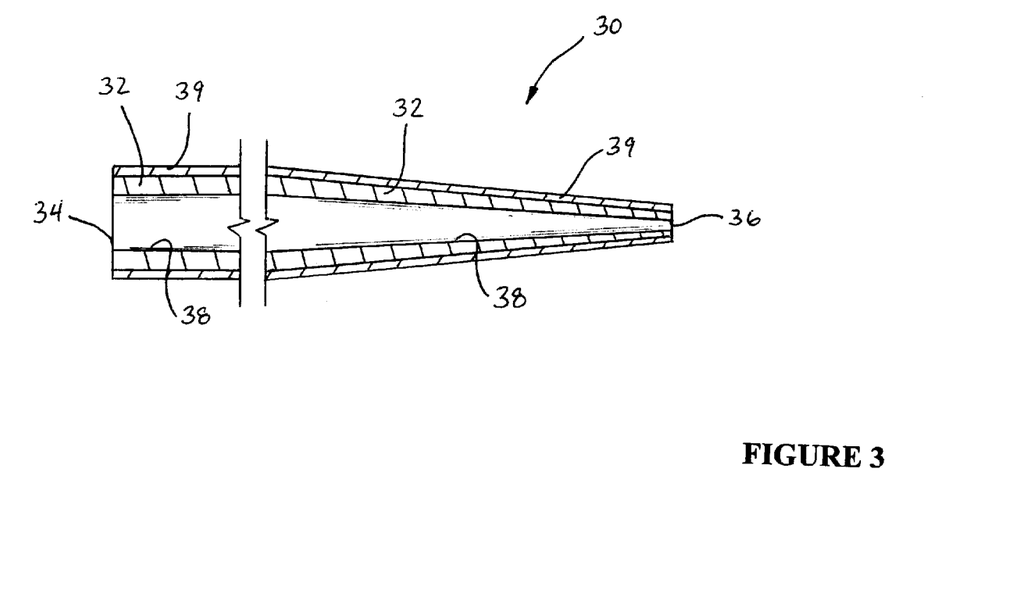
FIG. 3 is a longitudinal cross-sectional view of another embodiment of a PANI-coated nanospray emitter of the present invention. The PANI coating covers substantially the entire length of the emitter body (i.e., from the inlet to the outlet orifice).

A third embodiment of the nanospray emitter of the present invention is illustrated in FIG. 3. The emitter 30 includes a tapered (i.e., conical) body 32 having a fluid inlet 34, an outlet orifice 36, and a passage 38 communicating between the fluid inlet and outlet orifice. Adhered to substantially the entire exterior of the body 32 is a PANI coating 39, which extends from the proximal end containing the outlet orifice 36 to the distal end containing the inlet 24.

A further aspect of the present invention relates to a method of making a nanospray emitter of the present invention. Basically, the method is carried out by providing a nanospray emitter body which includes a fluid inlet, an outlet orifice, and a passage communicating between the fluid inlet and outlet orifice; and then casting a thin film of an electrically conductive polymer coating onto at least a portion of the nanospray emitter body.

The process step of casting can be achieved by a number of procedures.

According to a first approach, application of the conductive polymer coating can be carried out by dipping the portion of the emitter body into a soluble suspension which includes the conductive polymer. The soluble suspension can be either an aqueous suspension or in an organic solvent. After dipping, the solvent is allowed to evaporate, leaving behind the PANI coating on the portion of the emitter body dipped into the suspension.

When aqueous suspensions are employed, the PANI is preferably derivatized to ensure its solubility in water. A water soluble PANI derivative (Chen and Hwang, 1995) is commercially available from Monsanto (St. Louis, Mo.). Although PANI films cast from aqueous suspensions are susceptible to dissolution by some protic solvents, such PANI films are still functional for nanospray.

When organic suspensions are employed, a suitable organic solvent should be selected on the basis of its ability to form a soluble suspension of PANI without degradation of the quality of PANI film produced upon evaporation of the solvent. Suitable organic solvents include, without limitation, xylene and a mixture of xylene and a diacetone alcohol (e.g., 4-hydroxy-4-methyl-2-pentanone), typically in an approximate 1:1 ratio. Unlike PANI films cast from aqueous solutions, PANI films cast from xylene solutions are not susceptible to degradation by exposure to protic solvents. To preclude tackiness of the resulting PANI film, not more than about 5% by weight of PANI should be suspended in an organic solvent.

To ensure that the film resulting from the dipping process does not interfere with the outlet orifice, this first approach may also include the step of passing a fluid through the passage of the emitter body during the dipping step and, optionally, during the curing step. The fluid is preferably a gas, such as air, or a non-reactive gas, such as nitrogen.

To control the rate of deposition of the conductive polymer onto the emitter body (and, thus, control the thickness of the conductive polymer and its uniformity along the length of the emitter body), it may be desirable to utilize a device (e.g., a lab jack) which can be used to lower and raise the emitter body into the suspension containing the conductive polymer at a suitable rate. For PANI suspensions, the device can be used to withdraw the emitter body from the suspension at a rate of about 5 mm/s. This should achieve a PANI coating of suitable thickness.

According to a second approach, the step of casting can be carried out by polymerizing the conductive polymer onto the portion of the emitter body in an acidic solution by oxidation. By way of example, oxidative polymerization of aniline (0.10 M) can be carried out in aqueous solution by $(NH_4)_2S_2O_8$ (ammonium peroxydisulfate 0.1 M) treatment at ~0–5° C. in 1 M aqueous HCl, as described in earlier protocols (Chiang et al., 1986; MacDiarmid, 1987). Preferably, a vanadium oxide catalyst is utilized to afford consistent results from the polymerized films (MacDiarmid, 1987). A portion of the emitter body is dipped into the catalyzed solution to polymerize the film on the portion in the solution. The time length in which the emitter body is present in the catalyzed solution will affect the thickness of the resulting polymerized film. Typically, a time length of about 5 to about 60 minutes is sufficient, more preferably about 15 to about 20 minutes. The thicknesses of the electrically conductive film should be as set forth above.

Upon removal of the emitter body from the catalyzed solution, polymerization can be quenched by washing the emitters with aqueous $NH_4OH$ (Chiang et al., 1986; Fong and Schlenoff, 1995) Afterward, the emitters can be washed with 1 M HCl to ensure the film is in its conductive state, as indicated visually (for PANI, by a green film).

As noted above, a gas can be blown through the passage of the emitter body to prevent clogging of the outlet orifice by the polymer.

According to a third approach, the step of casting can be carried out by coating the portion of the emitter body in a solution containing a non-conductive base form of the conductive polymer, and then doping the coated emitter to produce a conductive polymer coating. By way of example, PANI film can be formed out of N-methyl-2-pyrrolidinone solution using commercially available PANI (Polysciences, Inc., Warrington, Pa.). Conductive PANI is immersed into basic solution (pH ~8) for several hours to produce the non-conductive emeraldine base form (structure I), which is soluble in N-methyl-2-pyrrolidinone. The N-methyl-2-pyrrolidinone is then doped with 1.0 M HCl (pH ~0) to produce the conductive form of PANI, or "emeraldine salt." The emitter substrate is dipped into the doped solution, then removed and dried. This coating procedure produces optically transparent PANI films that conduct electricity.

As noted above, a gas can be blown through the passage of the emitter body to prevent clogging of the outlet orifice by the polymer.

According to a fourth approach, the step of casting can be carried out by introducing the emitter body, or portion thereof, into an RF discharge chamber and then exposing the emitter body, or portion thereof, to aniline monomers under conditions effective to coat the portion of the emitter body with polyaniline.

By way of example, the emitter body can be introduced into an RF discharge chamber (Vargo et al., 1989; Vargo et al., 1991) along with aniline vapor (a few tenths of a torr) and exposed to RF discharge (about 50–100 kHz RF discharge frequency at about 10–50W) to deposit an electrically conductive PANI film on the surface of the emitter body (Bhat and Joshi, 1994; Cruz et al., 1997; Gong et al., 1998). Interestingly, Gong et al. showed that the physical and chemical properties of PANI films could be changed by altering the rf-plasma discharge conditions (Gong et al., 1998). With increasing discharge duration and rf-discharge power, the relative percentage of quinoid groups (relative to benzenoid) was increased, as was the degree of aliphatic cross-linking (Gong et al., 1998). However, the relative percentage of free radicals was found to be higher when lower rf-plasma powers were employed. Optionally, to enhance conductivity, the reaction chamber can be doped with iodine vapor (Bhat and Joshi, 1994) or the relative humidity can be increased (Cruz et al., 1997).

Having prepared an emitter of the present invention, it is intended to be used in a nano-electrospray device for creation of low sample volume nanosprays. Therefore, a further aspect of the present invention relates to a nano-electrospray device which includes a nanospray emitter of the present invention, as described above. The nano-electrospray device 40, illustrated in FIG. 4, includes a grounded emitter 10 of the present invention and a counter-electrode 42 connected to a power supply 44. The emitter 10 is supported by an emitter mount 44 such that the emitter can be coupled in fluid communication with a fluid source 50, which holds a fluid (containing one or more analytes) to be examined. During use of the nano-electrospray device, the solution delivered to the tip of the emitter body experiences the electric field associated with the maintenance of the tip at high potential. Assuming a positive potential, for example, positive ions in solution (i.e., in a condensed phase) will accumulate at the surface, which is drawn out in a downfield direction to establish a Taylor cone. At a high enough imposed electric field, the cone is drawn to a filament which produces positively charged droplets via a budding process when the surface tension is exceeded by the applied electrostatic force. As solution at the tip is dispersed into a gas phase (of the nanospray), additional fluid is drawn to the tip via capillary action. Thus, development of a suitable electrical potential between the counter-electrode 42 and the emitter 10 (i.e., through the electrically conductive polymeric coating on the emitter) causes the fluid to be drawn through the passage of the emitter for discharge from the outlet orifice by establishing an electrical field force which exceeds the surface tension of the fluid.

Although FIG. 4 shows the emitter being grounded and the counter-electrode connected to the power supply, it should be appreciated by one of skill in the art that a suitable electrical potential can also be activated by grounding the counter-electrode and coupling the emitter to the power supply.

Figure 4:
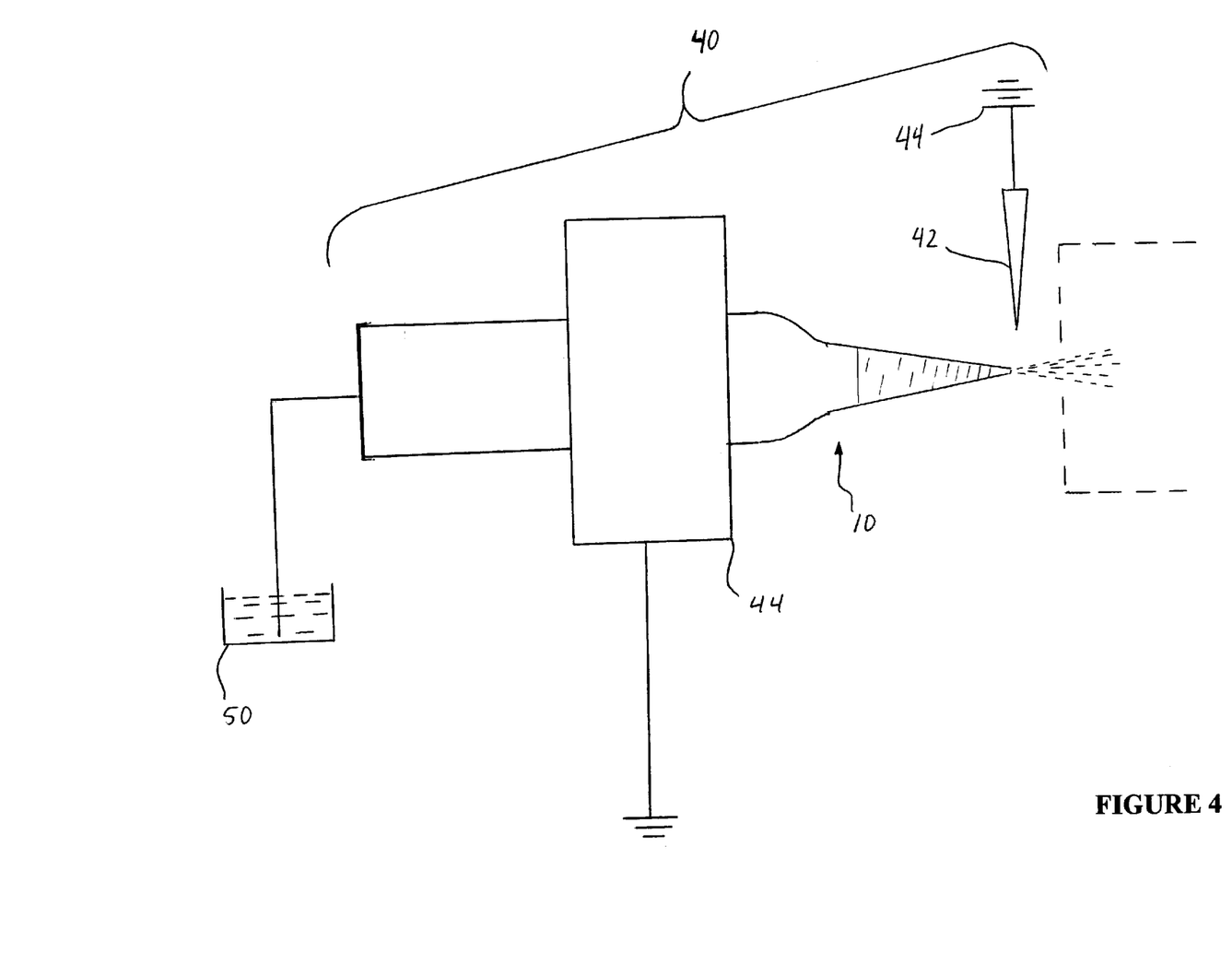
FIG. 4 illustrates an nano-electrospray device, including a counter-electrode coupled to a power supply and a grounded nanospray emitter whose inlet is in fluid communication with a fluid supply (i.e., containing a solution to be analyzed by MS).

The nano-electrospray device 40 is intended to be used in conjunction with any one of the following devices: a mass spectrometer, whose inlet can be coupled to receive the nanospray from the outlet orifice of the nano-electrospray device 40; liquid chromatography columns, whose outlet can be coupled to the inlet of the emitter on the nano-electrospray device 40; capillary electrophoresis columns, whose outlet can be coupled to the inlet of the emitter on the nano-electrospray device 40; and capillary electrochromatography columns, whose outlet can be coupled to the inlet of the emitter on the nano-electrospray device 40. One of skill in the art may readily appreciate that other equipment can readily be coupled to the nano-electrospray device 40 to introduce a fluid to be analyzed into the inlet thereof or to receive a nanospray from the outlet orifice thereof.

Thus, a further aspect of the present invention relates to a method of analyzing a solution for an analyte in the solution. This method is carried out by passing a solution including an analyte through a nanospray emitter of the present invention under conditions effective to electrically charge the solution in a manner to emit the solution from the emitter in the form of a nanospray, and then analyzing the nanospray emission in a manner suitable to detect an analyte present in the solution. Basically, the nanospray emission can be analyzed using now known or hereafter developed devices which are suitable for the intended analysis to be performed. For example, without being limited thereby, a mass spectrometer can receive the nanospray emission to identify one or more analytes in the nanospray emission.

With the use of a nano-electrospray device of the present invention, it is possible to determine the pharmacokinetic behavior of pharmaceutical agents, the behavior of endogenous biochemicals (e.g., neuropeptides, neurotransmitters, nucleic acids, proteins, other intercellular signaling molecules, etc.), or the interaction of pharmaceutical agents with endogenous biochemicals in the formation of drug complexes (e.g., drug-protein complexes).

EXAMPLES

The following examples are intended to be illustrative of the present invention, but are no means intended to the limit the scope thereof.

Materials & Instrumentation

The following materials were used in the Examples provided below:

water-soluble conductive PANI dispersions (5% aqueous, conductive form) was obtained from Monsanto (St. Louis, Mo.), where the water-soluble PANI is functionalized with proprietary tethers and is otherwise commercially available from Monsanto as PANAQUA (without the tethers, PANI is not soluble in water (Chen, 1995));

xylene-soluble conductive PANI dispersions ($M_w$ 117,000 Da, 48.16% xylenes, 12.62% butyl cellosolve, the remainder solid PANI) was obtained from Monsanto (St. Louis, Mo.);

polyethylene(glycol) ($M_n$ 1000, PEG-1000), poly(dimethylsiloxane) ($M_n$ 1250, PDMS-1250), and equine cytochrome c were obtained from Sigma; and methyl-terminated polyethylene(glycol) ($M_n$ 2000, ME PEG-2000) was obtained from Aldrich (Milwaukee, Wis.).

Electrospray ionization-mass spectra analysis were performed using the following instrumentation:

All ESI mass spectra were acquired using a 3 tesla Bruker Daltonics BioApex 30es (Billerica, Mass.) Fourier transform mass spectrometer equipped with an Analytica of Branford (Branford, Conn.) nanospray source. A metal cap (250 µm) was fitted over the capillary inlet to the mass spectrometer to reduce the diameter of the opening and to decrease the probability of electrical discharge stripping the conductive coating off the mass spectrometer's inlet capillary, making it functionally useless. PANI-coated nanospray emitters were inserted into the emitter mount (FIG. 4) and loaded with sample by the following means. A gas-tight Hamilton syringe containing the sample was connected to a union inlet by 1.5 cm length of fluorinated ethylene polymer (FEP) tubing (1/16" OD, 0.03" ID). A 3 cm segment of Polymicro Technologies (Phoenix, Ariz.) fused silica tubing (186 µm OD, 50 µm ID) connected to the outlet. The silica tubing was then inserted into the PANI-coated emitter to its taper, and sample was slowly injected using the syringe. In this way, the liquid analyte forms a plug without bubbles in the emitter tip. The PANI-coated emitter was held at ground and positioned to ~0.5–2 mm distance from the metal-capped capillary inlet to the mass spectrometer (as viewed from a microscope mounted on the nanospray source) using the micrometer on the nanospray source. The onset of nanospray was initiated with the counter-electrode at ~−650 V, and spray was conducted typically at −650 to −1200 V. Ions were accumulated in the external hexapole (Lau et al., 1997) and electrostatically injected into the Infinity cell (Caravatti and Allemann, 1991) (2.0 V trapping potential) using Sidekick (U.S. Pat. No. 4,924,089 to Caravatti). Frequency-sweep excitation from m/z 294 to 2400 was applied at an amplitude of ~30 $V_{pp}$. Detection was in direct mode (bandwidth 0–156250 Hz). The data sets were apodized with a Gaussian function, Fourier transformed, and displayed in magnitude mode using XMASS 4.0.2 on a Silicon Graphics (Mountain View, Calif.) RPC 4600 INDY data station.

Example 1

Preparation of Emitters Coated with Water-soluble PANI

Figure 5:
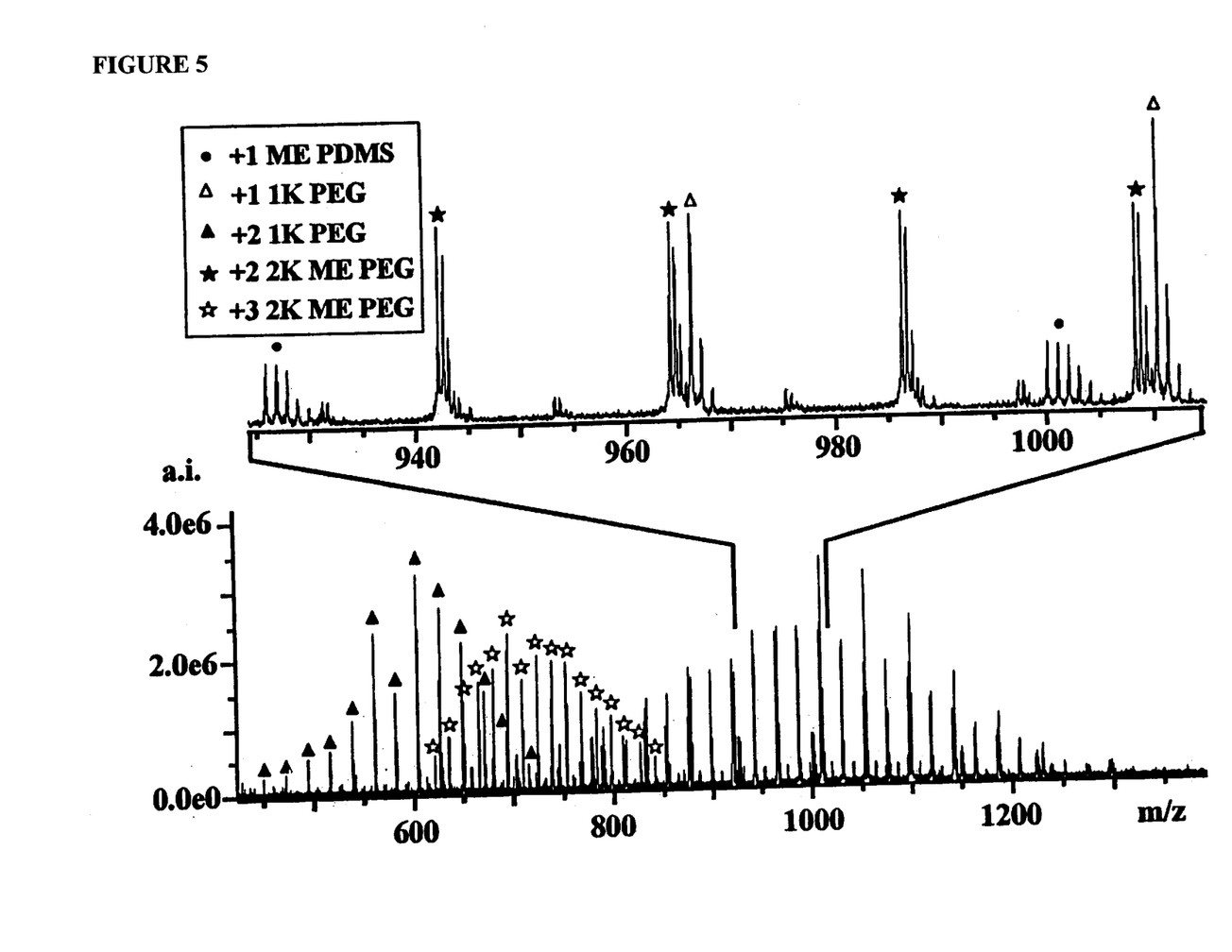
FIG. 5 is a nanospray ESI-Fourier transform mass spectrum ("FTMS") of the polymer mixture PEG-1000/PDMS-1250/methyl-terminated PEG 2000. The symbols that follow represent various polymer species: (Δ) singly-sodiated PEG-1000, (▲) doubly-sodiated PEG-1000, (★) doubly-sodiated PEG-2000, (☆) triply-sodiated PEG-2000, and (●) singly-sodiated PDMS-1250. Top inset: expansion of m/z region 910–1030.

Gold-coated and uncoated borosilicate glass emitters (1.2 mm OD, 0.69 mm ID) pulled to tapers for the ESI outlet with 4±1 µm ID were purchased directly from New Objective (Cambridge, Mass.). The uncoated emitters were gently swiped using the sealed end of a melting tube upon which aqueous conductive PANI had been applied while the emitter was rotated manually. Though this application method does not provide a PANI coating of uniform thickness, it is easy to confirm by visual inspection whether or not the ESI outlet is covered by a transparent green coating of PANI. A very low flow of air could be (but was not always) run through the emitter to prevent clogging of the emitter orifice during application of water-soluble PANI. The PANI-coated emitter was then allowed to air dry. Within three minutes, the PANI coating was sufficiently adherent to the substrate such that the emitter was usable for nanospray.

Photomicrographs (FIG. 1B) were obtained using a Nikon Optiphot confocal microscope in the Confocal Microscopy and 3-D Imaging Lab in the School of Medicine and Biomedical Sciences at SUNY-Buffalo.

Example 2

Performance of Emitters Coated with Water-soluble PANI

Nanospray was initiated with PANI-coated emitters when the counter-electrode voltage was between −600 and −1200

V. Because of the transparent green PANI coating over the emitter substrate (FIG. 1B), one could determine whether any air bubbles were present that might interfere with nanospray using a microscope. An example of nanospray (~40 nL/min flow rate) using the water-soluble PANI-coated emitters is shown in FIG. 5, which is a mixture of three synthetic polymers dissolved in methanol:2-propanol:10 mM NaOH (49:49:2, v/v/v): methyl-terminated PDMS ($M_n$ 1250), PEG ($M_n$ 1000), and methyl-terminated PEG ($M_n$ 2000). The NaOH was added to provide a cation source for creating PDMS ions. Singly- and doubly-charged oligomer ions of PEG-1000 and doubly- and triply-charged oligomer ions of methyl-terminated PEG-2000 are observed, as are singly-sodiated oligomer ions of PDMS. Similar results were obtained when xylene-soluble PANI was used.

Interestingly, normal flow ESI (i.e., no nanospray) of this same mixture reveals only the PEG distributions, and the PDMS is absent. In distinguishing it from nanospray, normal flow ESI is defined here as being performed with a metal needle, (grounded relative to counter-electrode held at −3 kV), 50 µm i.d., at 1 µL/min flow rate. Perhaps the higher surface area-to-liquid volume ratio of nanospray vs. normal ESI enables ionization and detection of the more hydrophobic PDMS. No evidence for any ion derived from PANI is found in the spectrum. Thus, PANI-coated nanospray emitters can be used without the worry of possible contamination from the PANI. In spite of the spectral complexity of the data for the three polymers in FIG. 5, the high mass resolving power of FTMS allows for easy identification of charge state (top inset) (Henry, 1991), while the ionic species' identities can be confirmed by high mass accuracy (Maziarz et al., 1999).

The PANI-coated emitter used for the sample in FIG. 5 maintained continuous spray for 40+ minutes before sample was exhausted. Inspection of this emitter under a microscope did not indicate any clear signs of degradation. This was actually somewhat surprising, since it was observed that PANI cast from water-soluble dispersions will dissolve in protic solvents (methanol, ethanol, and water), though such films are exceedingly stable in the presence of 2-propanol and acetonitrile. Of course, the fluid never comes in direct contact with the PANI film (save perhaps at the very edge of the tip). Thus, while some dissolution of the film might be expected if a protic solvent comes into direct contact with PANI cast from water-soluble dispersions, this has not yet prevented the tips from being durable.

A 50/50 mixture of methanol and 2-proponal was injected into the emitter and spray was reinitiated to rinse the emitter tip. The next day, this same emitter was used to collect nanospray mass spectra for numerous samples, with rinsing in-between. Even after running multiple samples over two days through the same PANI-coated emitter, stable signal could be obtained without electrical discharge and the emitter continued to be functional. Indeed, with rinsing in between sample loadings, the PANI-coated emitters can be reused many times. While such capability may not be needed for general sample analysis, the availability of stable emitters for coupling to sheathless CE-MS is still an analytical challenge (Lausecker et al., 1998). Thus, the current PANI-coated emitters may prove useful in coupling nanospray to CE-MS.

The emitters are extraordinarily stable to electrical discharge. Under normal operating conditions, no evidence of electrical arcing was observed (either by destruction of the PANI coating or from direct observation of the PANI tip). Arcing could only be induced when the counter-electrode voltage was set above −3 kV and when the tip was placed within 0.2 mm of the counter-electrode (indeed, arcing could only be guaranteed if the tip was inserted directly into the inlet hole in the counter-electrode). Gold-coated tips could be induced to arc at much lower voltages (~−1 kV) even 2 mm away from the counter-electrode.

Example 3

Preparation of Emitters with Xylene-soluble PANI

Gold-coated and uncoated borosilicate glass emitters (1.2 mm OD, 0.69 mm ID) pulled to tapers for the ESI outlet with 4±1 µm ID were purchased directly from New Objective (Cambridge, Mass.). The uncoated emitters were gently swiped using the sealed end of a melting tube upon which xylene conductive PANI had been applied while the emitter was rotated manually. The xylene conductive PANI suspension obtained from Monsanto (St. Louis, Mo.) was modified to reduce the PANI concentration to not more than about 5% by weight. Though this application method does not provide a PANI coating of uniform thickness, it is easy to confirm by visual inspection whether or not the ESI outlet is covered by a transparent green coating of PANI. A very low flow of air could be (but was not always) run through the emitter to prevent clogging of the emitter orifice during application of xylene-soluble PANI. The PANI-coated emitter was then allowed to air dry. Within three minutes, the PANI coating was sufficiently adherent to the substrate such that the emitter was usable for nanospray.

Example 4

Performance of Emitters Coated with Xylene-soluble PANI

As noted previously, PANI has high mechanical stability and anti-static properties (Trivedi and Dhawan, 1992). Part of the stability imparted by the PANI coating may be due to its thickness. PANI films cast from xylene-soluble dispersions, however, are insensitive to degradation by protic solvents.

Figure 6:
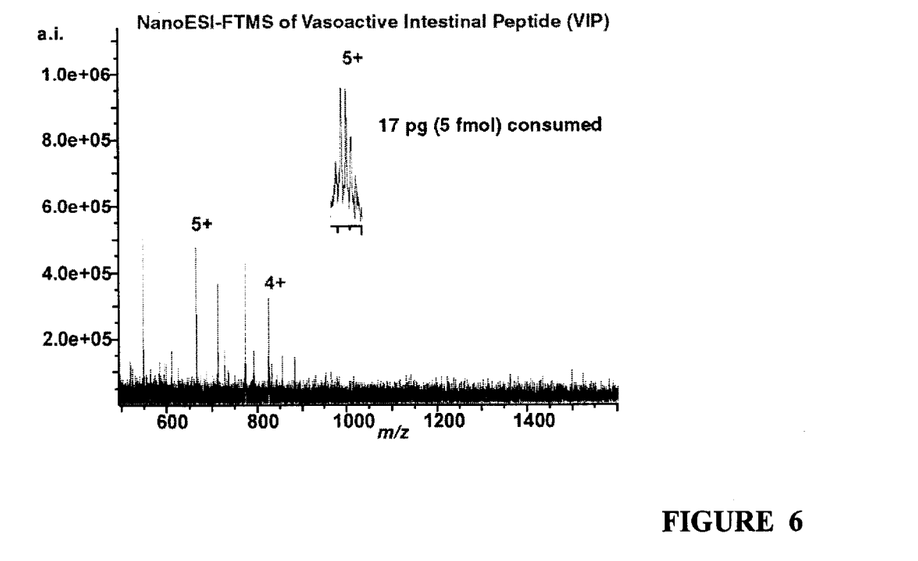
FIG. 6 is a nanospray FTMS spectrum of vasoactive intestinal peptide using PANI from xylene dispersions as the coating. Total peptide consumed: 5 femtomoles.

An example of the routine low detection limits achievable with PANI-coated nanospray emitters using an FTMS detector is shown in FIG. 6. Here, vasoactive intestinal peptide (VIP) (1 ng/µL in methanol/water/acetic acid 49/49/2) was electrosprayed at ~40 nL/min over 25 sec using a borosilicate nanospray emitter coated with a xylene-soluble dispersion of PANI. Thus, ~17 nL sample volume, or 17 picograms (5 femtomoles) of total peptide were used to acquire the ESI-FTMS spectrum in FIG. 6. Flow rate was determined by injecting 5 µL of sample and waiting until tip stops producing signal; for the tip used in FIG. 6, ~120 min.

Figure 7A:
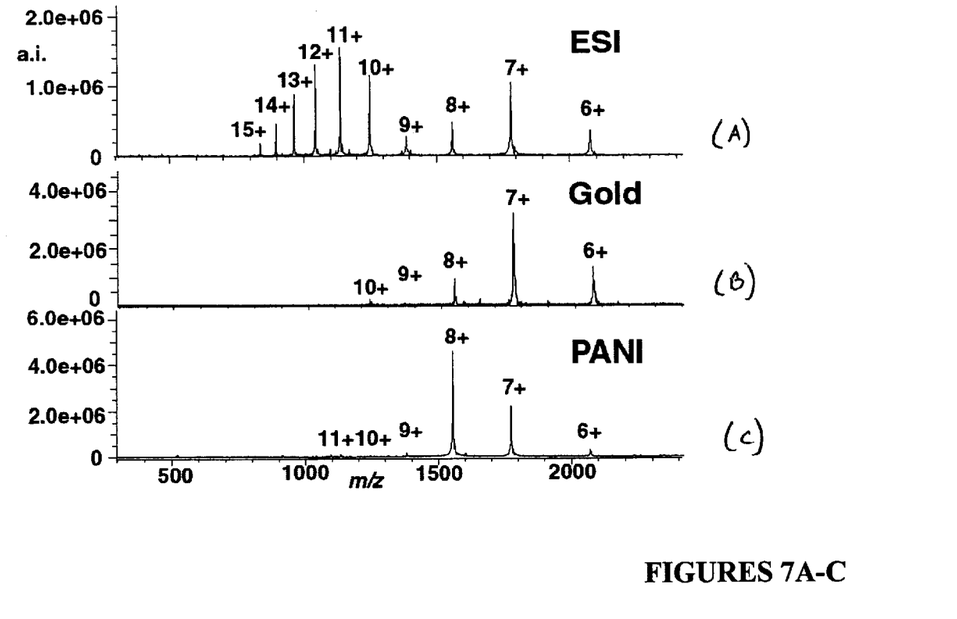
FIG. 7A is a normal ESI-FT mass spectrum, sum of 10 scans. Total sample consumed=17 pmol.

Use of PANI films cast from xylene-soluble dispersions with nanospray is shown in FIG. 7. FIG. 7a is an ESI-FT mass spectrum of equine cytochrome c (30 µM, 50/50 v/v methanol/water) using conventional ESI (flow rate=1 µL/min). The spectrum shown in FIG. 7b is nanospray of an identical cytochrome c solution using instead gold-coated nanospray emitters (flow rate ~100 nL/min). Using nanospray emitters coated with xylene-soluble PANI, the same sample (flow rate ~40 nL/min) generates the spectrum observed in FIG. 7c. The normal ESI spectrum reveals a multiplicity of charge states from 6+ to 15+, while the nanospray spectra reveal charge states over the range 6+ to 11+.

The discrepancy between charge state distributions for cytochrome c using conventional ESI and nanospray is not inherently obvious. One possibility is that ions are desolvated more quickly in nanospray than in ESI, thus ions spend more time in the "gas-phase" if formed from nanospray. Perhaps this results in increased charge stripping. Of course, another possibility is that conformational effects may limit charging of a protein, though it is not immediately clear why conformation should be any different for ions produced by nanospray vs. ESI.

One of the key attributes of low flow ESI that has been noted is its high sensitivity (Emmett and Caprioli, 1994; Kriger et al., 1995; Valaskovic et al., 1995a; Kelly et al., 1997; Wilm and Mann, 1996; Valaskovic et al., 1996a). The total amount of cytochrome c consumed to acquire the spectrum in FIG. 7a was 17 pmol, while only 1.3 pmol was required to obtain the spectrum in FIG. 7b (using gold-coated nanospray emitters) and 680 fmol to obtain the spectrum in FIG. 7c (using PANI-coated nanospray emitters). Thus, PANI-coated nanospray emitters show improved sensitivity (as do gold-coated emitters) vs. normal flow ESI. While the total signal and signal-to-noise ratios are superior with the PANI-coated emitter in FIG. 7c vs. the gold-coated emitter in FIG. 7b, it is likely this is due to the flow rate differences used to acquire the two spectra.

Example 5

Stability of PANI Films on Emitters

Figure 8A:
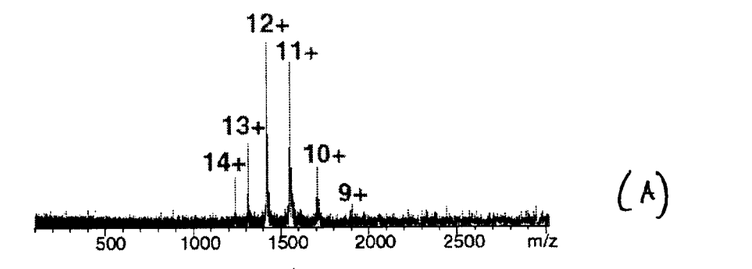
FIGS. 8A–B are aligned nanospray-FTMS of 29.2 μM myoglobin (49/49/2 methanol/water/glacial acetic acid, v/v/v) using a nanospray emitter that was coated with water-soluble PANI. Qualitatively, the same charge states are observed at both 5 min (top, FIG. 6A) or 160 min (bottom, FIG. 6B) after the initiation of nanospray, with slightly improved S/N observed at 160 min.
Figure 8B:
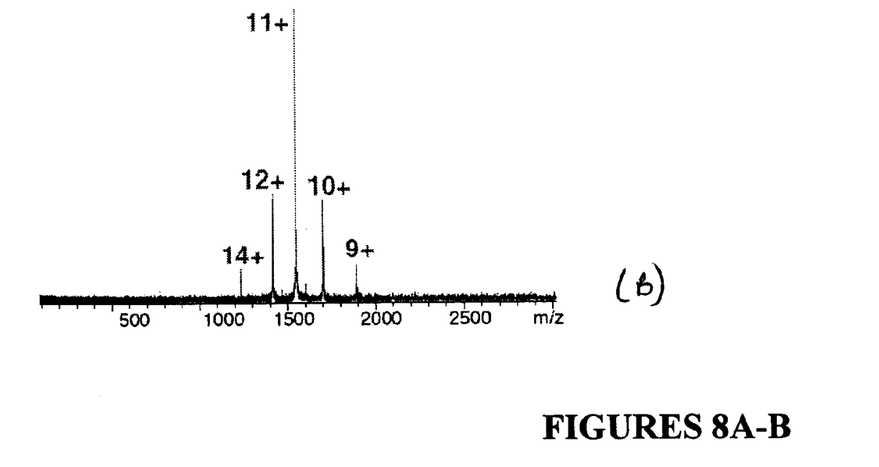

The durability of the PANI films for nanospray is also made evident in FIG. 8. Here, the same nanospray emitter is used to acquire nanospray-FT mass spectra of myoglobin over 160 minutes. In comparison to convention gold-coated emitters, the PANI coated emitters of the present invention were useful after far longer than the typical 15–30 minutes survival on the ESI-FTMS equipment utilized herein (which is consistent with their reported survival, Valaskovic et al., 1995a). Thus, this demonstration illustrates that nanospray emitters with PANI coatings have similar sensitivity yet superior durability to gold-coated emitters.

In addition, several types of cast PANI films exhibit solvent stability. As shown in Table 1 below, in general PANI films cast from water-soluble dispersions have much lower stability in protic solvents than those cast from xylene-soluble films. While degradation of the films by the naked eye is often difficult to detect, inspection via microscopy shows that solvent exposure can, in fact, dissolve PANI coatings at the emitter orifice in most cases. However, even when PANI films do dissolve upon solvent exposure, the PANI-coated nanospray emitters were still operable over a period of days, and could be reused many times. Films produced from PANI dispersions in xylene (Monsanto, Inc.) show stability to protic solvents, but prove to be very sticky at concentrations above 5% PANI by weight.

TABLE 1

Solvent Stabilities of PANI Films

| Solvent | Water-soluble PANI | Xylene-soluble PANI |
|---|---|---|
| water | dissolves immediately | stable over 24 h. |
| isopropanol | Stable for 10 min., slightly soluble after 20 h. | Slow dissolution, complete within 24 h. |
| ethanol | Forms suspension in minutes, complete dissolution after 20 h. | Stable over 24 h. |
| methanol | forms suspension in minutes | Stable over 24 h. |
| acetonitrile | Stable over 20 h. | Stable over 24 h. |
| glacial acetic acid | Stable for 10 min., but dissolves completely within 20 h. | Stable over 24 h. |

TABLE 1-continued

Solvent Stabilities of PANI Films

| Solvent | Water-soluble PANI | Xylene-soluble PANI |
|---|---|---|
| nitric acid (1 M) | dissolves immediately | Slight dissolution within 24 h. |
| sodium hydroxide (1.15 M) | PANI film turns blue, dissolves slowly, and will not produce stable ESI even if emitter is removed from solvent before dissolution | stable after 24 h., no color change |
| DMSO | dissolves immediately | Stable over 24 h. |

Example 6

Electrospray Ionization-Mass Spectral Analysis of Paclitaxel and Proposed Use of Nanospray ESI-LC/MS has proved valuable for drug development because of its ability to provide structural information and quantify the drug and its metabolites with lower detection limits than UV spectroscopy (Lee et al., 1997). For example, paclitaxel (taxol) is an alkaloid that has received considerable attention because of its efficacy in treating ovarian tumors (Suffness, 1995). Paclitaxel promotes tubulin polymerization and inhibits depolymerization, thereby inhibiting cell division in cancer cells (Parness et al., 1982). A sharpened picture of the mechanistic and metabolic pathways of paclitaxel may lead to improvements in its clinical efficacy (Dorr, 1997). Thus, in spite of FDA approval, further review of paclitaxel's biotransformation is still needed.

An HPLC assay of paclitaxel in mouse plasma using UV detection was developed by Sharma et al. (Sharma et al., 1994). This method can quantify paclitaxel for up to 4–8 h after I.V. injection. Adequate description of the pharmacokinetics requires quantification over a 24–36 h period. Such information from test subjects is currently unavailable. Information of this type would prove useful in determining dosage requirements and treatment frequency for cancer patients using paclitaxel in clinical trials.

ESI-MS and ionspray-MS have been used for structural characterization of paclitaxel and its metabolites (Poon et al., 1996; Volk et al., 1997; Lee et al., 1997; Kerns et al., 1995; Blay et al., 1993; Bitsch et al., 1993). The following ESI-MS protocol shall be used to analyze paclitaxel in mouse plasma samples. Paclitaxel is ESI stable in an 80% acetonitrile:20% ammonium acetate buffer solution at pH 3–7 (pH adjusted by adding acetic acid), and the presence of both monomeric and dimeric species has been noted. In fact, the paclitaxel dimer has also been observed under 95% water/5% acetonitrile conditions, which are much more like the in vivo conditions which would be found in patients. Indeed, the dimer may play a role in the bioactivity of paclitaxel (Balasubramanian et al., 1994).

By extending this work to nanospray, it is expected to lower these detection limits significantly so that paclitaxel can be detected over the entire course of a 24–36 h blood plasma pharmacokinetics study. Thus, the nanospray emitters described here may be used to detect in vivo levels of paclitaxel and its metabolites. This is especially important because, to date, no determination has been achieved on the presence of in vivo levels of the paclitaxel dimer, which may play a significant role in the polymerization of tubulin proteins to form microtubules. In addition, since sodiated paclitaxel dimer is the dominant dimeric species, nanospray can be used to examine whether high (mM) levels of sodium salts further enhance dimerization. Such studies would be virtually impossible with ESI since high salt concentrations make ESI virtually unusable; however, nanospray is much more tolerant of such high salt concentrations.

List of References Cited

Each of the references cited above and listed below is hereby incorporated by reference in its entirety.

Balasubramanian, S. V.; Alderfer, J. L.; Straubinger, R. M. Solvent- and Concentration-Dependent Molecular Interactions of Taxol (Paclitaxel), *J. Pharm. Sci.* 1994, 83, 1470–1476 ("Balasubramanian et al., 1994").

Banks, J. F., Jr. Separation and Analysis of Proteins by Perfusion Liquid Chromatography and Electrospray Ionization Mass Spectrometry. *J. Chromatogr. A* 1995, 691, 325–330 ("Banks, 1995").

Bhat, N. V.; Joshi, N. V. Structure and properties of plasma-polymerized thin films of polyaniline, *Plasma Chem. Plasma Process.* 1994, 14, 151–161 ("Bhat and Joshi, 1994").

Bitsch, F.; Ma, W.; Macdonald, F.; Nieder, M.; Shackleton, C. H. L. Analysis of Taxol and Related Diterpenoids from Cell Cultures by Liquid Chromatography-Electrospray Mass Spectrometry, *J. Chromatogr. B* 1993, 615, 273–280 ("Bitsch et al., 1993").

Blay, P. K. S.; Thibault, P.; Thiberge, N.; Kiechen, B.; Debrun, A.; Mercure, C. Analysis of Taxol and Related Taxanes from Taxus Canadensis Using Liquid Chromatography Combined with Mass Spectrometry or Tandem Mass Spectrometry, *Rapid Commun. Mass Spectrom.* 1993, 7, 626 ("Blay et al., 1993").

Cao, P.; Moini, M. A novel sheathless interface for capillary electrophoresis/electrospray ionization mass spectrometry using an in-capillary electrode. *J. Am. Soc. Mass Spectrom.* 1997, 8, 561–564 ("Cao and Moini, 1997").

Caravatti, P.; Allemann, M. The "Infinity Cell": a New Trapped-ion Cell With Radiofrequency Covered Trapping Electrodes for Fourier Transform Ion Cyclotron Resonance Mass Spectrometry. *Org. Mass Spectrom.* 1991, 26, 514–518 ("Caravatti and Allemann, 1991").

Chen, S.-A.; Hwang, G.-W. Water-soluble self-acid-doped conducting polyaniline: structure and properties. *J. Am. Chem. Soc.* 1995, 117, 10055–10062 ("Chen and Hwang, 1995").

Chiang, J.-C.; MacDiarmid, A. G. 'Polyaniline': protonic acid doping of the emeraldine base form to the metallic regime, *Synth. Met.* 1986, 13, 193–205 ("Chiang et al., 1986").

Cruz, G. J.; Morales, J.; Castillo-Ortega, M. M.; Olayo, R. Synthesis of polyaniline films by plasma polymerization, *Syn. Met.* 1997, 88, 213–218 ("Cruz et al., 1997").

Dorr, R. T. Pharmacology of the taxanes, *Pharmacotherapy* 1997, 17, 96S-104S ("Dorr, 1997").

Emmett, M. R.; Caprioli, R. M. Micro-electrospray mass spectrometry: ultra-high-sensitivity analysis of peptides and proteins. *J. Am. Soc. Mass Spectrom.* 1994, 5, 605–613 ("Emmett and Caprioli, 1994").

Emmett, M. R.; White, F. M.; Hendrickson, C. L.; Shi, S. D.-H.; Marshall, A. G. Application of Micro-Electrospray Liquid Chromatography Techniques to FT-ICR MS to Enable High-Sensitivity Biological Analysis. *J. Am. Soc. Mass Spectrom.* 1998, 9, 333–340 ("Emmett et al., 1998").

Fong, Y.; Schlenoff, J. B. Polymerizers of aniline using mixed oxidizers, *Polymer* 1995, 36, 639–643 ("Fong and Schlenoff, 1995").

Fong, K. W. Y.; Chan, T.-W. D. A Novel Nonmetallized Tip for Electrospray Mass Spectrometry at Nanoliter Flow Rate. *J. Am. Soc. Mass Spectrom.* 1999, 10, 72–75 ("Fong and Chan, 1999").

Genies, E. M.; Boyle, A.; Lapkowiski, M.; Tsintavis, C. Polyaniline: a historical survey, *Synth. Met.* 1990, 36, 139–182 ("Genies et al., 1990").

Gong, X. Y.; Dai, L.; Mau, A. W. H.; Griesser, H. J. Plasma-polymerized polyaniline films: synthesis and characterization, *J. Polym. Sci., Polym. Chem. Part A* 1998, 36, 633–643 ("Gong et al., 1998").

Hannis, J. C.; Muddiman, D. C. Nanoelectrospray Ionization using Tapered (50→10 $\mu$m) Non-Metalized Fused Silica Capillaries. *Rapid Commun. Mass Spectrom.* 1998, 12, 443–448 ("Hannis et al., 1998").

Henry, K. D.; Quinn, J. P.; McLafferty, F. W. High-Resolution Electrospray Mass Spectra of Large Molecules. *J. Am. Chem. Soc.* 1991, 113, 5447–5449 ("Henry et al., 1991 ").

Kelleher, N. L.; Senko, M. W.; Siegel, M. M.; McLafferty, F. W. Unit resolution mass spectra of 112 kDa molecules with 3 Da accuracy. J. Am. Soc. Mass Spectrom. 1997, 8, 380–383 ("Kelleher et al., 1997").

Kelly, J. F.; Ramaley, L.; Thibault, P. Capillary zone electrophoresis-electrospray mass spectrometry at submicroliter flow rates: practical considerations and analytical performance. *Anal. Chem.* 1997, 69, 51–60 ("Kelly et al., 1997").

Kerns, E. H.; Volk, K. J.; Hill, S. E.; Lee, M. S. Profiling New Taxanes Using LC/MS and LC/MS/MS Substructural Analysis Techniques, *Rapid Commun. Mass Spectrom.* 1995, 9, 1539–1545 ("Kerns et al., 1995").

Kriger, M. S.; Cook, K. D.; Ramsey, R. S. Durable Gold-Coated Fused Silica Capillaries for Use in Electrospray Mass Spectrometry. *Anal. Chem.* 1995, 67, 385–389 ("Kriger et al., 1995").

Lau, R. L. C.; Jiang, J.; Ng, D. K. P.; Chan, T.-W. D. Fourier transform ion cyclotron resonance studies of lanthanide (III) porphyrin-phthalocyanine heteroleptic sandwich complexes using electrospray ionization. *J. Am. Soc. Mass Spectrom.* 1997, 8, 161–169 ("Lau et al., 1997").

Lausecker, B.; Hopfgartner, G.; Hesse, M. Capillary electrophoresis-mass spectrometry coupling versus micro-high-performance liquid chromatography-mass spectrometry coupling: a case study. *J. Chromatogr. B* 1998, 718, 1–13 ("Lausecker et al., 1998").

Lee, M. S.; Kerns, E. H.; Hail, M. E.; Liu, J.; Volk, K. J. Recent applications of LC-MS techniques for the structure identification of drug metabolites and related compounds, *LC•GC* 1997, 15, 542–558 ("Lee et al., 1997").

MacDiarmid, A. D.; Chiang, J. C.; Richter, A. F.; Epstein, A. J. Polyaniline: A New Concept in Conducting Polymers. *Synth. Met.* 1987, 18, 285–190 ("MacDiarmid et al., 1987").

Manohar, S. K.; MacDiarmid, A. D.; Epstein, A. J. Pernigraniline, an isolable intermediate in the conventional chemical synthesis of emeraldine. *Synth. Met.* 1991, 41–43, 711–714 ("Manohar et al., 1991").

Maziarz, E. P., III; Baker, G. A.; Wood, T. D. Capitalizing on the high mass accuracy of ESI-FTMS for synthetic polymer characterization: a detailed investigation of poly (dimethylsiloxane). *Macromolecules* 1999, 32, 4411–4418 ("Maziarz et al., 1999").

Meng, C. K.; Mann, M.; Fenn, J. B. Of Protons or Proteins. *Z. Phys. D* 1988, 10, 361–368 ("Meng et al., 1988").

Parness, J.; Kingston, D. G. I.; Powell, R. G.; Harracksingh, C.; Horwitz, S. B. Structure-Activity Study of Toxicity and Microtubule Assembly In Vitro by Taxol and Related Taxanes, *Biochem. Biophys. Res. Commun.* 1982, 105, 1082–1089 ("Parness et al., 1982").

Poon, G. K.; Wade, J.; Bloomer, J.; Clarke, S. E.; Maltas, J. Rapid Screening of Taxol Metabolites in Human Microsomes by Liquid Chromatography/Electrospray Ionization-Mass Spectrometry, *Rapid Commun. Mass Spectrom.* 1996, 10, 1165–1168 ("Poon et al., 1996").

Schmeer, K.; Behnke, B.; Bayer, E. Capillary Electrochromatography-Electrospray Mass Spectrometry: A Microanalysis Technique. *Anal. Chem.* 1995, 67, 3656–3658 ("Schmeer et al., 1995").

Sharma, A.; Conway, W. D.; Straubinger, R. M. Reversed-phase High-performance Liquid Chromatographic Determination of Taxol in Mouse Plasma, *J. Chromatogr. B* 1994, 655, 315–319 ("Sharma et al., 1994").

Smith, R. D.; Wahl, J. H.; Goodlett, D. R.; Hofstadler, S. A. Capillary Electrophoresis/Mass Spectrometry. *Anal. Chem.* 1993, 65, 574A–584A ("Smith et al., 1993").

Suffness, M., Ed.; *Taxol Science and Applications*; CRC Press, Inc.: Boca Raton, 1995, pp 426 ("Suffness, 1995").

Trivedi, D. C.; Dhawan, S. K. Grafting of Electronically Conducting Polyaniline on Insulating Surfaces. *J. Mat. Chem.* 1992, 2, 1091–1096 ("Trivedi and Dhawan, 1992")

Valaskovic, G. A.; Kelleher, N. L.; Little, D. P.; Aaserud, D. J.; McLafferty, F. W. Attomole Sensitivity Electrospray Source for Large Molecule Mass Spectrometry. *Anal. Chem.* 1995, 67, 3802–3805 ("Valaskovic et al., 1995a").

Valaskovic, G. A.; Holton, M.; Morrison, G. H. Parameter control, characterization, and optimization in the fabrication of optical fiber near-field probes, *Appl. Opt.* 1995, 34, 1215–1228 ("Valaskovic et al., 1995b").

Valaskovic, G. A.; Kelleher, N. L.; McLafferty, F. W. Attomole Protein Characterization by Capillary Electrophoresis-Mass Spectrometry. *Science* 1996, 273, 1199–1202 ("Valaskovic et al., 1996a").

Valaskovic, G. A.; McLafferty, F. W. Long-Lived Metallized Tips for Nanoliter Electrospray Mass Spectrometry. *J. Am. Soc. Mass Spectrom.* 1996, 7, 1270–1272 ("Valaskovic et al., 1996b").

Vargo, T. G.; Gardella, J. A., Jr.; Salvati, L., Jr. Multitechnique surface spectroscopic studies of plasma modified polymers III: $H_2O$ and $O_2/H_2O$ plasma modified poly (methyl methacrylates), *J. Polym. Sci., Part A, Polym. Chem.* 1989, 27, 1267–1286 ("Vargo et al., 1989").

Vargo, T. G.; Gardella, J. A., Jr.; Meyer, A. E.; Baier, R. E. Radio frequency glow discharge hydrolysis/oxidation of expanded poly tetra fluoro ethylene (ePTFE) and poly vinylidene difluoride (PVDF) surfaces, *J. Polym. Sci. Part A, Polym. Chem.* 1991, 29, 555–570 ("Vargo et al., 1991").

Volk, K. J.; Hill, S. E.; Kerns, E. H.; Lee, M. S. Profiling degradants of paclitaxel using liquid-chromatography-mass spectrometry and liquid chromatography-tandem mass spectrometry, *J. Chromatogr. B* 1997, 696, 99–115 ("Volk et al., 1997").

Wessling, B.; Posdorfer, J. Corrosion prevention with an organic metal (polyaniline): corrosion test results. *Electrochim. Acta* 1999, 44, 2139–2147 ("Wessling and Posdorfer, 1999").

Whitehouse, C. M.; Dreyer, R. N.; Yamashita, M.; Fenn, J. B. Electrospray interface for liquid chromatographs and mass spectrometers. *Anal. Chem.* 1985, 57, 675–679 ("Whitehouse et al., 1985").

Wilm, M.; Mann, M. Electrospray and Taylor-cone theory, Dole's beam of macromolcules at last? *Int. J. Mass Spectrom. Ion Processes* 1994, 136, 167–180 ("Wilm and Mann, 1994").

Wilm, M.; Mann, M. Analytical properties of the nanoelectrospray ion source. *Anal. Chem.* 1996, 68, 1–8 ("Wilm and Mann, 1996").

U.S. Pat. No. 4,924,089 to Caravatti, P.

Although the invention has been described in detail for the purposes of illustration, it is understood that such detail is solely for that purpose, and variations can be made therein by those skilled in the art without departing from the spirit and scope of the invention which is defined by the following claims.

What is claimed:

1. A nanospray emitter comprising:
   an emitter body formed of an electrically non-conductive material, the emitter body comprising a fluid inlet, an outlet orifice, and a passage communicating between the fluid inlet and outlet orifice; and
   an electrically conductive polyaniline coating on at least a portion of the emitter body.

2. The nanospray emitter according to claim 1, wherein the electrically non-conductive material comprises a glass or glass ceramic material.

3. The nanospray emitter according to claim 2, wherein the glass or glass ceramic material is a borosilicate, aluminosilicate, or fused silica material.

4. The nanospray emitter according to claim 1, wherein the emitter body is tapered toward the outlet orifice.

5. The nanospray emitter according to claim 1, wherein the outlet orifice has an inner diameter of less than about 20 µm.

6. The nanospray emitter according to claim 5, wherein the outlet orifice has an inner diameter of between about 1 µm to about 5 µm.

7. The nanospray emitter according to claim 1, wherein the nanospray emitter is translucent.

8. The nanospray emitter according to claim 1, wherein the conductive polymer coating has a substantially uniform thickness of less than about 10 µm.

9. The nanospray emitter according to claim 8, wherein the electrically conductive polymer coating has a substantially uniform thickness of between about 2 µm to about 4 µm.

10. The nano spray emitter according to claim 1, wherein the electrically conductive polymer coating comprises an electrical conductivity of between about $1.0 \times 10^{-3}$ to about 5 S/cm at 25° C.

11. The nano spray emitter according to claim 1, wherein the portion of the emitter body covered by the electrically conductive polymer is adjacent the outlet orifice, adjacent the inlet, or substantially the entire emitter body.

12. The nanospray emitter according to claim 11, wherein the portion of the emitter body covered by the electrically conductive polymer is adjacent the inlet.

13. The nanospray emitter according to claim 11, wherein the portion of the emitter body covered by the electrically conductive polymer is adjacent the outlet orifice.

14. A nano-electrospray device comprising:
   a counter-electrode and
   a nanospray emitter according to claim 1 whose inlet is capable of fluid communication with a fluid source including a fluid containing one or more analytes,
   wherein either the counter-electrode or the nanospray emitter can be coupled to a power supply, with the other being grounded, for development of a suitable electrical potential between the counter-electrode and the nanospray emitter, which causes the fluid to be drawn through the passage of the nanospray emitter for discharge from the outlet orifice.

15. The nano-electrospray device according to claim 14, wherein the electrically non-conductive material comprises a glass or glass ceramic material.

16. The nano-electrospray device according to claim 14, wherein the emitter body is tapered toward the outlet orifice.

17. The nano-electrospray device according to claim 14, wherein the outlet orifice has an inner diameter of less than about 20 µm.

18. The nano-electrospray device according to claim 14, wherein the nanospray emitter is translucent.

19. The nano-electrospray device according to claim 14, wherein the conductive polymer coating has a substantially uniform thickness of less than about 10 µm.

20. The nano-electrospray device according to claim 14, wherein the electrically conductive polymer coating comprises an electrical conductivity of between about $1.0 \times 10^{-3}$ to about 5 S/cm at 25° C.

21. The nanospray emitter according to claim 14, wherein the portion of the emitter body covered by the electrically conductive polymer is adjacent the outlet orifice, adjacent the inlet, or substantially the entire emitter body.

22. A method for making a durable nanospray emitter, comprising:
providing a nano spray emitter body formed of an electrically non-conductive material, the nanospray emitter body comprising a fluid inlet, an outlet orifice, and a passage communicating between the fluid inlet and outlet orifice,
casting a thin film of an electrically conductive polyaniline coating onto at least a portion of the nanospray emitter body.

23. The method according to claim 22, wherein the electrically non-conductive material comprises a glass or glass ceramic.

24. The method according to claim 22, wherein said casting comprises:
polymerizing the conductive polymer onto the portion of the emitter body in an acidic solution by oxidation.

25. The method according to claim 22, wherein said casting comprises:
coating the portion of the emitter body in a solution containing a non-conductive base form of the conductive polymer; and
doping the coated emitter to produce a conductive polymer coating.

26. The method according to claim 22, wherein said casting comprises:
dipping the portion of the emitter body into a soluble suspension comprising the conductive polymer.

27. The method according to claim 26, wherein the soluble suspension comprises the conductive polymer in water.

28. The method according to claim 26, wherein the soluble suspension comprises the conductive polymer in xylene or a solvent comprising xylene.

29. The method according to claim 26, further comprising:
passing a fluid through the passage of the emitter body during said dipping.

30. The method according to claim 29, wherein the fluid is a gas.

31. The method according to claim 29, wherein the fluid is a non-reactive gas.

32. The method according to claim 22, wherein said casting comprises:
introducing the emitter body, or portion thereof, into an RF discharge chamber and
exposing the emitter body, or portion thereof, to aniline monomers under conditions effective to coating the portion of the emitter body with polyaniline.

33. A method of forming a nanospray of a solution comprising:
passing a solution comprising an analyte through a nanospray emitter according to claim 1 under conditions effective to electrically charge the solution in a manner to emit the solution from the emitter in the form of a nanospray.

34. A method of analyzing a solution for an analyte in the solution, the method comprising:
passing a solution comprising an analyte through a nanospray emitter according to claim 1 under conditions effective to electrically charge the solution in a manner to emit the solution from the emitter in the form of a nanospray; and
analyzing the nanospray emission in a manner suitable to detect an analyte present in the solution.

35. The method according to claim 34, wherein the analyte is a drug, an endogenous biochemical, or a drug-protein complex.

* * * * *